United States Patent [19]

Effland et al.

[11] Patent Number: 4,970,219
[45] Date of Patent: Nov. 13, 1990

[54] HETEROARYLAMINO-AND HETEROARYLOXYPYRIDINAMINE COMPOUNDS WHICH HAVE USEFUL UTILITY IN TREATING SKIN DISORDERS

[75] Inventors: Richard C. Effland; Joseph T. Klein, both of Bridgewater; Gordon E. Olsen, Somerset; Larry Davis, Sergeantsville, all of N.J.

[73] Assignee: Hoechst-Roussel Pharmaceuticals Inc., Somerville, N.J.

[21] Appl. No.: 372,509

[22] Filed: Jun. 28, 1989

[51] Int. Cl.$^5$ .................. A61K 31/44; C07D 213/36
[52] U.S. Cl. ................................. 514/339; 546/273
[58] Field of Search ............... 514/349, 352, 353, 339; 546/273

[56] References Cited

U.S. PATENT DOCUMENTS

| | | | |
|---|---|---|---|
| 3,118,884 | 1/1964 | Clarke | 544/106 |
| 3,495,969 | 2/1970 | Driscoll | 71/94 |
| 3,576,616 | 4/1971 | Nowotny | 546/326 |
| 3,681,366 | 8/1972 | Bebenburg et al. | 546/308 |
| 3,721,676 | 3/1973 | Witzel et al. | 546/307 |

FOREIGN PATENT DOCUMENTS

| | | | |
|---|---|---|---|
| 0069885 | 9/1987 | Australia | 546/111 |
| 0110405 | 6/1984 | European Pat. Off. | 546/307 |
| 2073736 | 10/1981 | United Kingdom | 546/307 |

OTHER PUBLICATIONS

Brewster et al., J. Heterocyclic Chem., vol. 15, (1975), pp. 1497–1499.
Bulter et al., J. Med. Chem., vol. 24, 1981, pp. 346–350.
Ito et al., Chem. Pharm. Bull., vol. 26, No. 5, 1978, pp. 1375–1383.

*Primary Examiner*—Mary C. Lee
*Assistant Examiner*—Zinna Northington-Davis
*Attorney, Agent, or Firm*—Tatsuya Ikeda

[57] ABSTRACT

There are described compounds of the formula where
n is 0 or 1;
X is O or $NR_2$, $R_2$ being hydrogen, loweralkyl or loweralkylcarbonyl;
R is hydrogen, loweralkyl, arylloweralkyl or loweralkylcarbonyl; and $R_1$ is wherein $R_3$ is hydrogen, loweralkyl or loweralkylcarbonyl;

which compounds are useful as topical antiinflammatory agents for the treatment of various dermatoses.

26 Claims, No Drawings

HETEROARYLAMINO- AND HETEROARYLOXYPYRIDINAMINE COMPOUNDS WHICH HAVE USEFUL UTILITY IN TREATING SKIN DISORDERS

The present invention relates to compounds of Formula I,

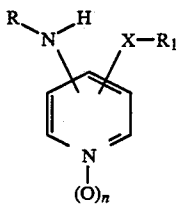
(I)

where
n is 0 or 1;
X is O or $NR_2$, $R_2$ being hydrogen, loweralkyl or loweralkylcarbonyl;
R is hydrogen, loweralkyl, arylloweralkyl or loweralkylcarbonyl; and
$R_1$ is

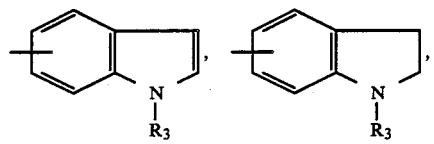

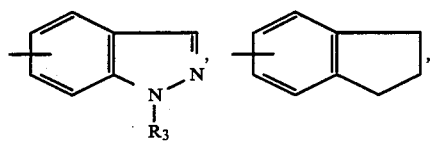

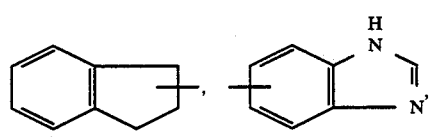

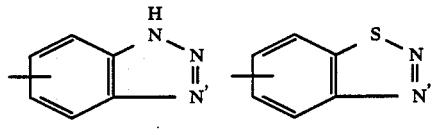

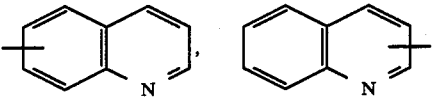

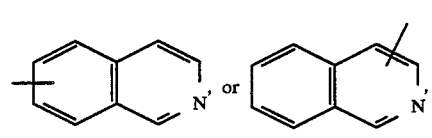

wherein $R_3$ is hydrogen, loweralkyl or loweralkylcarbonyl;
which compounds are useful as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Also included within the scope of this invention are compounds of Formula II where n, X and $R_1$ are as defined above, which are useful for the same dermatological applications as mentioned above and also as direct precursors of the compounds of Formula I.

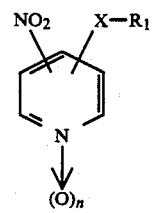
(II)

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group optionally mono-substituted with a loweralkyl, loweralkoxy, halogen or trifluoromethyl group.

Throughout the specification and the appended claims, a given chemical formula or name shall encompass all stereo, optical, geometrical and tautomeric isomers where such isomers exist.

The compounds of this invention are prepared by utilizing one or more of the synthetic steps described below.

Throughout the description of the synthetic steps, the notations R, $R_1$, $R_2$, $R_3$, X and n shall have the respective meanings given above unless otherwise stated or indicated, and other notations shall have the respective meanings defined in their first appearances unless otherwise stated or indicated.

STEP A:
A compound of Formula III where Hal is F or Cl, preferably F, is allowed to react with a compound of Formula IV where M is Na, K or Li to afford a compound of Formula V.

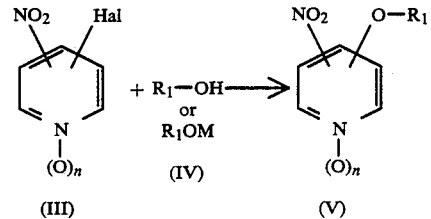

This reaction is typically conducted in a suitable solvent such as ethanol, dimethylformamide, dimethylsulfoxide or N-methylpyrrolidone at a temperature of about 0° to 150° C.

3-Fluoro-4-nitropyridine-N-oxide, which belongs to the group of compounds of Formula III, is disclosed in Talik and Talik, Roczniki Chemii, Volume 38, 777 (1964). 4-Chloro-3-nitropyridine, which also belongs to the group of compounds of Formula III, is disclosed in Talik, et al., Roczniki Chemii, Volume 43(5), 923 (1969).

STEP B:

Compound III is allowed to react with a compound of Formula VI to afford a compound of Formula VII.

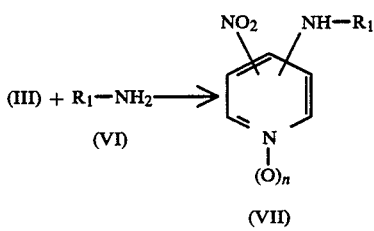

This reaction is typically conducted in the presence of a suitable solvent such as ethanol, dimethylformamide, dimethylsulfoxide or N-methylpyrrolidone at a temperature of about 0° to 150° C.

STEP C:

Compound VII is allowed to react with a compound of the formula, $R_2$-Hal, where $R_2$ is loweralkyl, aryl-loweralkyl or loweralkylcarbonyl and Hal is bromine or chlorine in a routine manner known to the art to afford a compound of Formula VIII.

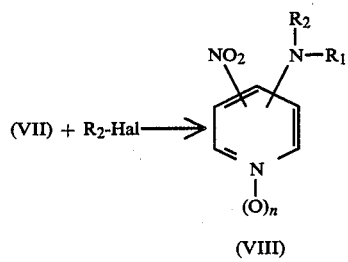

STEP D:

A compound of Formula IX which is obtained from STEP A, B or C is selectively hydrogenated to afford a compound of Formula X.

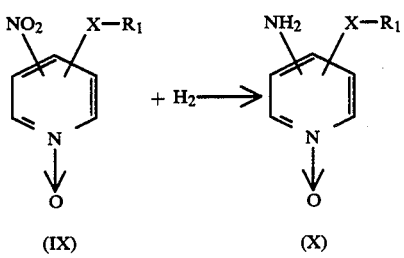

This selective hydrogenation is typically conducted with the aid of a suitable catalyst such as Pd/C or $PtO_2$ and a suitable medium such as ethanol at a temperature of about 20° to 80° C.

STEP E:

Compound IX is catalytically hydrogenated in a manner similar to the one described in STEP D above, except that a longer reaction period or higher reaction temperature is preferably employed, to afford a compound of Formula XI.

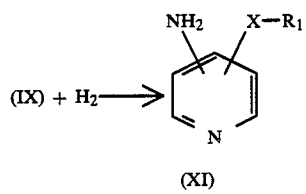

Instead of using compound IX in the above reaction, one can also use compound X and conduct the hydrogenation in substantially the same manner as described above to obtain compound XI.

STEP F:

A compound of Formula XII obtained from STEP D or E is allowed to react with a compound of the formula, $R_4$-Hal, where $R_4$ is loweralkyl, arylloweralkyl or loweralkylcarbonyl and Hal is bromine or chlorine, in a routine manner known to the art to afford a compound of Formula XIII.

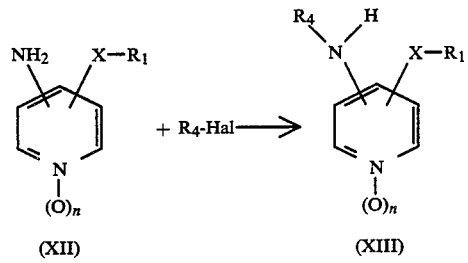

Compounds of Formula I and Formula II according to this invention are useful as topical agents for the treatment of various skin disorders such as those mentioned earlier. The dermatological activities of the compounds of this invention were ascertained with reference to the following methods.

DERMATOLOGICAL TEST METHODS

Phospholipase $A_2$-induced Paw Edema (PIPE)

The ability of compounds to prevent naja naja (snake venom) phospholipase $A_2$-induced paw edema in male Wistar rats (100–125 g) was measured. $PLA_2$ (3 units/paw) alone or with 0.1M of the test compound was injected in the subplantar region of the rat left hindpaw. Immediately subsequent to the injection and at two hours post administration the paw was immersed in a mercury bath, and paw displacement was measured on a recorder via a transducer. (Standard: hydrocortisone $ED_{50}=0.46M$). See Giessler, A. J. et al., Agents and Actions, Vol. 10, Trends in Inflammation Research (1981), p. 195.

In Vitro Phospholipase $A_2$ Assay ($PLA_2$)

The ability of a compound to modulate $PLA_2$ activity (cleavage of $^{14}C$-dipalmitoyl phosphotidylcholine at the 2-position to $^{14}C$-palmitic acid) was quantitated in this assay. The reaction mixture contained Tris buffer (25 mM), pH 8.0, calcium chloride (2.0 mM), bovine serum albumin (0.5 mg), dipalmitoyl phosphotidylcholine ($8 \times 10^{-5}M$), ($^{14}C$-palmitoyl)dipalmitoyl phosphotidylcholine ($6 \times 10^3$ cpm), porcine pancreatic $PLA_2$ (3.2 units) and the test compound. The reaction was run at 37° C. in a shaking incubator. The reaction was quenched and an internal standard was added in order to determine sample recovery. The samples were loaded onto $C_{18}$ columns, eluted with ethanol, and the radioactivity was then measured. (Standard: quinacrine $IC_{50}=3.5\times 10^{-4}M$). See Feyen, J.H.M., et al., *Journal of Chromatography* 259 (1983), pp. 338-340.

Arachidonic Acid-Induced Ear Edema (AAEE)

The purpose of this assay was to determine the ability of a topically-applied compound to prevent mouse ear edema induced by topical application of arachidonic acid. Female Swiss Webster mice topically received vehicle or test compound (1.0 mg/ear) on both ears (10 μl on outer and inner ears). After 30 minutes, the right ear of all groups received arachidonic acid (4 mg/ear) and the left ear received vehicle alone. After an additional 1 hour, the mice were sacrificed and an ear punch (4 mm) was taken from each ear. The difference in right and left ear punch weights for each animal was determined to assess activity. (Standard: indomethacin $ED_{50}=1.5$ mg/ear). See Young, J. M. et al., *Invest. Dermatol.*, 80, (1983), pp 48-52.

TPA-Induced Ear Edema (TPAEE)

The purpose of this assay was to determine the ability of a topically-applied compound to prevent ear edema induced by topical application of TPA (phorbol 12-myristate acetate). Female Swiss Webster mice topically received TPA (10 μg/ear) on the right ear and vehicle on the left ear. The test compound (10 μg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50}=47$ μg/ear). See Young, J. M. et al., *J. Invest. Dermatol.*, 80 (1983), pp. 48-52.

Cultured Human Keratinocyte DNA Synthesis (in vitro DNA)

The effect of a compound on the proliferation of cultured human epidermal keratinocytes was measured. After incubation with a test compound for 24 hours, the cultures were pulse-labelled for three hours with 5 μCi of $^3$H-thymidine. The cultures were extracted for DNA successively with trichloroacetic acid and ethanol, and thereafter dissolved with NaOH. The radioactive incorporation of $^3$H-thymidine into DNA was determined. (Standard: indomethacin $IC_{50}=3.8\times 10^{-5}M$).

Epidermal DNA Synthesis (in vivo DNA)

The influence of compounds on the proliferation of skin was assessed by determining inhibition or stimulation of DNA synthesis. HRS/J hairless mice received topical application of a compound or vehicle alone on the dorsal aspect. After 24 hours, $^3$H-thymidine (25 μCi) was administered by intraperitoneal injection. After an additional hour, animals were sacrificed and the dorsal skin was removed. The epidermal layer was peeled from the dermis by heat separation. Unincorporated $^3$H-thymidine was removed by washing successively with trichloroacetic acid and ethanol. Samples were centrifuged at 2,000 rpm and supernatants discarded. The epidermal sheets were then extracted with warm trichloroacetic acid and the supernatants analyzed for $^3$H-thymidine incorporation by scintillation counting and total DNA by a standard colorimetric assay. (Standard: indomethacin $ED_{50}=1.75$ mg/animal). See Lowe, N.J., et al., Arch. Dermatol., 117 (1981), pp. 394-8; and Burton, K., *Biochem. J.* 62 (1956), pp. 315-22.

Dermatological activities for some of the compounds of this invention are presented in Table 1.

TABLE 1

| Compound | PIPE* (0.1 M) | PLA$_2$* (0.01 M) | AAEE (1 mg) | TPAEE (10 μg) | in vivo DNA (2.5 mg) | in vitro DNA (50 μM) |
|---|---|---|---|---|---|---|
| N-(4-Nitro-3-pyridinyl)-1H-indol-5-amine, N$^5$-oxide | | −71% | | | | |
| 1-Methyl-N-(4-nitro-3-pyridinyl)-1H-indol-5-amine, N$^5$-oxide | −41% | −66% | | −30% | | |
| N-(3-Nitro-4-pyridinyl)-1H-indol-5-amine | | −36% | | | | |
| N-(4-Nitro-3-pyridinyl)-1H-indol-7-amine, N$^7$-oxide | | | | −40% | | |
| N-(4-Nitro-3-pyridinyl)-1H-indazol-5-amine, N$^5$-oxide | | | | −78% | | |
| N-(4-Nitro-3-pyridinyl)-1H-indazol-6-amine, N$^6$-oxide | | −83% | | | | |
| N-(Indan-5-yl)-4-nitro 3-pyridinamine-1-oxide | | | | −44% | −48% | |

TABLE 1-continued

| Compound | PIPE* (0.1 M) | PLA$_2$* (0.01 M) | AAEE (1 mg) | TPAEE (10 μg) | in vivo DNA (2.5 mg) | in vitro DNA (50 μM) |
|---|---|---|---|---|---|---|
| N-(Indan-1-yl)-4-nitro-3-pyridinamine-1-oxide | | | | −65% | | |
| N-(4-Amino-3-pyridinyl)-1H-indol-5-amine | −67% | −87% | −41% | −85% | −27% | −81% |
| N-(4-Amino-3-pyridinyl)-1-methyl-1H-indol-5-amine | −42% | −62% | | | | |
| N-(3-Amino-4-pyridinyl)-1H-indol-5-amine | | −82% | −37% | | | |
| 3-[(1H-Indol-5-yl)-oxy]-4-pyridinamine | −62% | −34% | −50% | −42% | −37% | |
| 1-Acetyl-N-(4-amino-3-pyridinyl)-2,3-dihydro-1H-indol-5-amine | | | −36% | | | |
| 4-[(1H-Indol-5-yl)-oxy]-3-pyridinamine | −52% | | | | | |
| N$^3$-(Indan-5-yl)-3,4-pyridinediamine | | | −49% | −75% | | |
| N-(4-Amino-3-pyridinyl)-1H-indol-7-amine, N$^7$-oxide | −45% | | | −38% | | |
| N-(4-Amino-3-pyridinyl)-1H-indazol-6-amine | −57% | −35% | | | | |

*difference in edema vs. control

Examples of the compound of this invention include:
N-(4-Amino-3-pyridinyl)-1H-indol-5-amine;
N-(4-Amino-3-pyridinyl)-1-methyl-1H-indol-5-amine;
N-(3-Amino-4-pyridinyl)-1H-indol-5-amine;
3-[(1H-Indol-5-yl)oxy]-4-pyridinamine;
1-Acetyl-N-(4-amino-3-pyridinyl)-2,3-dihydro-1H-indol-5-amine;
4-[(1H-Indol-5-yl)oxy]-3-pyridinamine;
N$^3$-(Indan-5-yl)-3,4-pyridinediamine;
N-(4-Amino-3-pyridinyl)-1H-indazol-5-amine;
N-(4-Amino-3-pyridinyl)-1H-indol-7-amine, N$^7$-oxide;
N-(4-Amino-3-pyridinyl)-1H-indol-7-amine;
N-(4-amino-3-pyridinyl)-1H-indazol-6-amine;
N-(4-Nitro-3-pyridinyl)-1H-indol-5-amine, N$^5$-oxide;
1-Methyl-N-(4-nitro-3-pyridinyl)-1H-indol-5-amine, N$^5$-oxide;
N-(3-Nitro-4-pyridinyl)-1H-indol-5-amine;
N-(4-Nitro-3-pyridinyl)-1H-indol-7-amine, N$^7$-oxide;
1-Acetyl-2,3-dihydro-N-(4-nitro-3-pyridinyl)-1H-indole-5-amine, N$^5$-oxide;
N-(4-Nitro-3-pyridinyl)-1H-indazol-5-amine, N$^5$-oxide;
N-(4-Nitro-3-pyridinyl)-1H-indazol-6-amine, N$^6$-oxide;
N-(Indan-5-yl)-4-nitro-3-pyridinamine-1-oxide;
N-(Indan-1-yl)-4-nitro-3-pyridinamine-1-oxide;
5-[(4-Nitro-3-pyridinyl)oxy]-1H-indole, N$^5$-oxide;
5-[(3-nitro-4-pyridinyl)oxy]-1H-indole;

The following examples are presented in order to illustrate this invention:

EXAMPLE 1

N-(4-Nitro-3-pyridinyl)-1H-indol-5-amine, N$^5$-oxide

A solution of 3-fluoro-4-nitropyridine-1-oxide[1] (5 g) and 1H-indol-5-amine (4.2 g) in 100 ml ethanol was warmed to 80° for one hour and thereafter cooled, and the product was filtered to give 8 g solid, d 244°. Three grams were recrystallized from acetonitrile to give 2.6 g solid, d 244°–245°.

[1] Talik and Talik, Roczniki Chemii 38, 777 (1964).

| ANALYSIS | | | |
|---|---|---|---|
| Calculated for C$_{13}$H$_{10}$N$_4$O$_3$ | 57.77% C | 3.73% H | 20.74% |
| Found | 57.99% C | 3.66% H | 20.91% N |

EXAMPLE 2

1-Methyl-N-(4-nitro-3-pyridinyl)-1H-indol-5-amine, N$^5$-oxide

A solution of 3-fluoro-4-nitropyridine-1-oxide (6 g) and 1-methyl-1H-indol-5-amine (5.5 g) in 125 ml ethanol was warmed on a steam bath for thirty minutes and thereafter cooled, diluted with ether and filtered to give 10 g solid, d 232°–234°. Three grams were recrystallized from ethanol to give 2.2 g needles, d 237°–238°.

| ANALYSIS | | | |
|---|---|---|---|
| Calculated for $C_{14}H_{12}N_4O_3$ | 59.15% C | 4.25% H | 19.71% N |
| Found | 59.31% C | 4.20% H | 19.71% N |

EXAMPLE 3

N-(3-Nitro-4-pyridinyl)-1H-indol-5-amine

To 150 ml of absolute ethanol were added 1H-indol-5-amine (8.06 g), 4-chloro-3-nitropyridine (10.0 g) and triethylamine (8.5 ml), and this mixture was heated to 60° C. and stirred for 2 hours. The mixture was cooled, the ethanol evaporated, and the residue taken up in a water/ethyl acetate mixture. This was treated with $Na_2CO_3$ (aq) to adjust the pH to 10. The organic layer was collected, the aqueous layer extracted again with ethyl acetate, and the organics were combined, washed with water and dried (sat. NaCl, anh. $MgSO_4$).

After filtration, the solvent was evaporated to yield a solid (14.2 g) which was eluted with 5% ethyl acetate/DCM on a silica gel column via flash method. The desired fractions were concentrated to yield a solid (6.1 g). Of this material, 2.0 g was recrystallized from absolute ethanol to yield a solid, 1.2 g, m.p. 204°–206° C.

| ANALYSIS | | | |
|---|---|---|---|
| Calculated for $C_{13}H_{10}N_4O_2$ | 61.41% C | 3.96% H | 22.04% N |
| Found | 61.41% C | 3.96% H | 22.00% N |

EXAMPLE 4

N-(4-Nitro-3-pyridinyl)-1H-indol-7-amine, $N^7$-oxide

To 200 ml ethanol were added 3-fluoro-4-nitropyridine-1-oxide (6.0 g) and 1H-indol-7-amine (5.5 g). After stirring at 85° C. for four hours, the mixture was cooled, and the precipitate was collected, washed with methanol, and dried at 60° C. overnight to give 9.9 g of solid, m.p. 250° C.

| ANALYSIS | | | |
|---|---|---|---|
| Calculated for $C_{13}H_{10}N_4O_3$ | 57.78% C | 3.73% H | 20.73% N |
| Found | 57.37% C | 3.54% H | 20.40% N |

EXAMPLE 5

1-Acetyl-2,3-dihydro-N-(4-nitro-3-pyridinyl)-1H-indole-5-amine, $N^5$-oxide

A solution of 3-fluoro-4-nitropyridine-1-oxide (4.5 g) and 1-acetyl-2,3-dihydro-1H-indol-5-amine (5 g) in 100 ml ethanol was stirred for two hours at reflux, and thereafter cooled and filtered to give 8.5 g crystals, d 239°–240°. Four grams were recrystallized from acetonitrile/ether to give 3 g crystals, d 255°–256°.

| ANALYSIS | | | |
|---|---|---|---|
| Calculated for $C_{15}H_{14}N_4O_4$ | 57.32% C | 4.49% H | 17.83% N |
| Found | 57.26% C | 4.49% H | 17.69% N |

EXAMPLE 6

N-(4-Nitro-3-pyridinyl)-1H-indazol-5-amine, $N^5$-oxide

A mixture of 3-fluoro-4-nitropyridine-1-oxide (6 g) and 1H-indazol-5-amine (5.2 g) in 150 ml of ethanol was refluxed for two hours, and thereafter was cooled, diluted with ether and filtered to give 10 g solid. A 3.5 g portion was recrystallized from ethanol to give 3.0 g solid, d 250°.

| ANALYSIS | | | |
|---|---|---|---|
| Calculated for $C_{12}H_9N_5O_3$ | 53.13% C | 3.34% H | 25.83% N |
| Found | 52.84% C | 3.34% H | 25.36% N |

EXAMPLE 7

N-(4-Nitro-3-pyridinyl)-1H-indazol-6-amine, $N^6$-oxide

To 100 ml of ethanol were added 3-fluoro-4-nitropyridine-1-oxide (6.0 g) and 1H-indazol-6-amine (5.5 g) and this mixture was heated to 70° C. and stirred for four hours. The mixture was filtered to yield a solid (9.5 g) which was recrystallized from methanol to yield a solid, 6.0 g, m.p. 247°–248° C. (decomposed).

| ANALYSIS | | | |
|---|---|---|---|
| Calculated for $C_{12}H_9N_5O_3$ | 53.14% C | 3.34% H | 25.82% N |
| Found | 52.96% C | 3.17% H | 25.72% N |

EXAMPLE 8

N-(Indan-5-yl)-4-nitro-3-pyridinamine-1-oxide

A solution of 3-fluoro-4-nitropyridine-1-oxide (12 g) and indan-5-amine (10 g) in 200 ml ethanol was stirred at reflux for two hours, and thereafter cooled, diluted with ether and filtered to give 19 g solid, m.p. 195°. Four grams were recrystallized from ethanol to give 2.6 g crystals, m.p. 194°–195°.

| ANALYSIS | | | |
|---|---|---|---|
| Calculated for $C_{14}H_{13}N_3O_3$ | 61.98% C | 4.83% H | 15.49% N |
| Found | 62.01% C | 4.89% H | 15.42% N |

EXAMPLE 9

N-(Indan-1-yl)-4-nitro-3-pyridinamine-1-oxide

A solution of 3-fluoro-4-nitropyridine-1-oxide (5.6 g) and indan-1-amine (6 g) in 100 ml ethanol was stirred at reflux for one hour and thereafter cooled and concentrated to 12 g of solid. This solid was purified by flash chromatography (silica, 10% ethyl acetate in dichloromethane) to give 9.2 g solid, m.p. 137°–138°. An analytical sample was obtained by recrystallizing 2.7 g from ethanol to give 2.5 g crystals, m.p. 141°–142°.

| ANALYSIS | | | |
|---|---|---|---|
| Calculated for $C_{14}H_{13}N_3O_3$ | 61.98% C | 4.83% H | 15.49% N |
| Found | 62.11% C | 4.89% H | 15.59% N |

EXAMPLE 10

5-[(4-Nitro-3-pyridinyl)oxy]-1H-indole, $N^5$-oxide

A solution of 5-hydroxyindole (4.8 g) in 20 ml dimethylformamide was slowly added to an ice cooled suspension of sodium hydride (0.9 g) in 5 ml dimethylformamide. After the anion formation, a solution of 3-fluoro-4-nitropyridine-1-oxide (5.7 g) in 20 ml dimethylformamide was added. After one hour the reaction mixture was stirred with ice water, extracted with chloroform and filtered. The organic extract was washed with water and saturated sodium chloride solution, dried (anhy. MgSO$_4$), filtered and concentrated to 3.5 g oil. This oil was purified by flash chromatography (silica, 20% ethyl acetate in dichloromethane) to give 2.2 g solid, d 208°–210°. This was combined with 2 g product obtained from another condensation and recrystallized from ethanol to give 3 g, d 216°–218°.

| ANALYSIS | | | |
|---|---|---|---|
| Calculated for C$_{13}$H$_9$N$_3$O$_4$ | 57.57% C | 3.34% H | 15.49% N |
| Found | 57.41% C | 3.36% H | 15.39% N |

EXAMPLE 11

5-[(3-nitro-4-pyridinyl)oxy]-1H-indole

To a solution of 5-hydroxyindole (7.45 g) in 100 ml of DMF was added K$_2$CO$_3$ (10.4 g). This mixture was stirred for 10 minutes at room temperature and then a solution of 4-chloro-3-nitropyridine (11.89 g) in 50 ml DMF was added dropwise. The reaction was allowed to proceed for 24 hours at room temperature. The mixture was poured into water and extracted with ethyl acetate. The organic layer was washed with water and saturated NaCl solution and dried over MgSO$_4$. After filtration, the solvent was evaporated to yield an oil (15.4 g). This material was eluted with 5% ethyl acetate/DCM on a silica gel column via HPLC. The desired fractions were concentrated to yield a solid, 1.35 g, m.p. 182°–184° C.

EXAMPLE 12

N-(4-Amino-3-pyridinyl)-1H-indol-5-amine

A mixture of N-(4-nitro-3-pyridinyl)-1H-indol-5-amine, N$^5$-oxide (7.8 g) in 500 ml ethanol containing platinum oxide (1.25 g) was hydrogenated at 50 psi for six hours and thereafter filtered and concentrated. The product was purified by flash chromatography (silica, 20% methanol in dichloromethane) to give 6 g solid, m.p. 83°–90°. Three grams were distilled twice via Kugelrohr (240°–250° @ 0.01 mm Hg) to give 2.4 g solid, 138°–140°.

| ANALYSIS | | | |
|---|---|---|---|
| Calculated for C$_{13}$H$_{12}$N$_4$ | 69.62% C | 5.39% H | 24.99% N |
| Found | 69.21% C | 5.47% H | 24.80% N |

EXAMPLE 13

N-(4-Amino-3-pyridinyl)-1-methyl-1H-indol-5-amine

A suspension of 1-methyl-N-(4-nitro-3-pyridinyl)-1H-indol-5-amine, N$^5$-oxide (6.8 g) in 250 ml ethanol containing 0.4 g platinum oxide was hydrogenated at 50 psi for twenty hours and thereafter filtered through Celite and concentrated to 3.5 g oil. This oil was purified by HPLC (silica 20% methanol in ethyl acetate) to give 2.5 g solid, m.p. 167°–169°. This solid was recrystallized from acetonitrile/ether to give 1.1 g solid, m.p. 168°–169°.

| ANALYSIS | | | |
|---|---|---|---|
| Calculated for C$_{14}$H$_{14}$N$_4$ | 70.57% C | 5.92% H | 23.51% N |
| Found | 70.44% C | 5.96% H | 23.39% N |

EXAMPLE 14

N-(3-Amino-4-pyridinyl)-1H-indol-5-amine

To a slurry of 10% Pd/C (1.0 g) in 10 ml of methanol was added N-(3-nitro-4-pyridinyl)-1H-indol-5-amine (4.0 g) in 230 ml methanol and this mixture was hydrogenated at 50 psi on a Parr apparatus. When the reaction was complete, the mixture was filtered through Celite and the filtrate concentrated to yield a solid (3.9 g). This material was eluted with 20% methanol/DCM on a silica gel column via HPLC. The desired fractions were concentrated to yield a solid (2.45 g) which was recrystallized from ethanol/water (10:1) to yield a solid, 1.8 g, m.p. 159°–161° C.

| ANALYSIS | | | |
|---|---|---|---|
| Calculated for C$_{13}$H$_{12}$N$_4$ | 69.62% C | 5.39% H | 24.98% N |
| Found | 69.63% C | 5.46% H | 25.07% N |

EXAMPLE 15

3-[(1H-Indol-5-yl)oxy]-4-pyridinamine

A suspension of 5-[(4-nitro-3-pyridinyl)oxy]-1H-indole, N$^5$-oxide (10 g) in 250 ml ethanol containing 0.4 g PtO$_2$ was hydrogenated at 50 psi for 25 hours and thereafter filtered through Celite and concentrated to 9 g oil. This oil was purified by HPLC (silica, 10% methanol in ethyl acetate) to give 3.5 g solid. This solid was recrystallized from acetonitrile to give 2.4 g crystals, m.p. 170°–172°.

| ANALYSIS | | | |
|---|---|---|---|
| Calculated for C$_{13}$H$_{11}$N$_3$O | 69.32% C | 4.92% H | 18.65% N |
| Found | 69.28% C | 4.80% H | 18.57% N |

EXAMPLE 16

1-Acetyl-N-(4-amino-3-pyridinyl)-2,3-dihydro-1H-indol-5-amine

A suspension of 1-acetyl-2,3-dihydro-N-(4-nitro-3-pyridinyl)-1H-indole-5-amine, N$^5$-oxide (13 g) in 250 ml ethanol containing 0.5 g PtO$_2$ was hydrogenated for two days at 60 psi and thereafter filtered through Celite and concentrated to 9 g solid. This solid was purified by HPLC (silica, 20% methanol in ethyl acetate) to give 4 g solid. This was combined with 1 g product obtained from a previous reduction and again purified by HPLC (silica, 20% methanol in ethyl acetate) to give 5 g solid, m.p. 210°–212°. This solid was recrystallized from acetonitrile to give 4 g solid, m.p. 212°–214°.

| ANALYSIS | | | |
|---|---|---|---|
| Calculated for C$_{15}$H$_{16}$N$_4$O | 67.15% C | 6.01% H | 20.88% N |
| Found | 66.84% C | 5.95% H | 20.80% N |

EXAMPLE 17

4-[(1H-Indol-5-yl)oxy]-3-pyridinamine

To a slurry of 10% Pd/C (1.0 g) in 10 ml of ethanol was added 5-[(3-nitro-4-pyridinyl)oxy]-1H-indole (3.7 g) in 240 ml ethanol and this was shaken on a Parr apparatus for 1 hour. The mixture was filtered and the filtrate concentrated to yield an oil (3.1 g) which was eluted with ethyl acetate on a silica gel column via HPLC. The desired fractions were concentrated to an oil which solidified on standing to yield 2.6 g, m.p. 155°–157° C.

| ANALYSIS | | | |
|---|---|---|---|
| Calculated for $C_{13}H_{11}N_3O$ | 69.32% C | 4.92% H | 18.65% N |
| Found | 69.13% C | 4.94% H | 18.46% N |

EXAMPLE 18

$N^3$-(Indan-5-yl)-3,4-pyridinediamine

A solution of N-(indan-5-yl)-4-nitro-3-pyridinamine-1-oxide (10 g) in 250 ml ethanol containing 0.4 g $PtO_2$ was hydrogenated at 60 psi for 24 hours and thereafter filtered through Celite and concentrated to 10 g oil. This oil was purified by flash chromatography (silica, 5% methanol in ethyl acetate) to give 8.3 g thick oil. This oil was crystallized in diethyl ether to give 5.5 g solid, m.p. 109°–110°.

| ANALYSIS | | | |
|---|---|---|---|
| Calculated for $C_{14}H_{15}N_3$ | 74.64% C | 6.71% H | 18.65% N |
| Found | 74.81% C | 6.72% H | 18.71% N |

EXAMPLE 19

N-(4-Amino-3-pyridinyl)-1H-indazol-5-amine

A suspension of N-(4-nitro-3-pyridinyl)-1H-indazol-5-amine, $N^5$-oxide (7 g) in 250 ml ethanol containing 0.5 g platinum oxide was hydrogenated at 60 psi for sixty hours and thereafter filtered through Celite and concentrated to 3.3 g solid. This solid was purified by HPLC (silica, 25% methanol in dichloromethane) to give 2.1 g solid. This solid was recrystallized twice from acetonitrile to give 1.5 g crystals, m.p. 198°–199°.

| ANALYSIS | | | |
|---|---|---|---|
| Calculated for $C_{12}H_{11}N_5$ | 63.98% C | 4.92% H | 31.10% N |
| Found | 63.66% C | 4.88% H | 30.94% N |

EXAMPLE 20

N-(4-Amino-3-pyridinyl)-1H-indol-7-amine, $N^7$-oxide

To 250 ml ethanol in a 500 ml Parr hydrogenation bottle were added N-(4-nitro-3-pyridinyl)-1H-indol-7-amine, $N^7$-oxide (5.0 g) and 0.4 g $PtO_2$. After shaking at ambient temperature for twenty-two hours under fifty psi hydrogen, the mixture was filtered and concentrated to a foam, 4.8 g.

This foam was eluted on a silica gel column with 30% methanol/DCM via HPLC. The desired fractions were combined and concentrated to a solid, 2.8 g, m.p. >250° C.

| ANALYSIS | | | |
|---|---|---|---|
| Calculated for $C_{13}H_{12}N_4O$ | 64.99% C | 5.03% H | 23.32% N |
| Found | 64.57% C | 5.12% H | 22.78% N |

EXAMPLE 21

N-(4-Amino-3-pyridinyl)-1H-indol-7-amine

To 250 ml ethanol in a 500 ml Parr hydrogenation bottle, were added N-(4-amino-3-pyridinyl)-1H-indol-7-amine, $N^7$-oxide (2.8 g) and 0.3 g $PtO_2$. The mixture was shaken at ambient temperature under fifty psi hydrogen for one hour, and thereafter filtered and concentrated to an oil, (2.7 g). This oil was eluted on a silica gel column with 30% methanol/DCM via HPLC. The desired fractions were combined and concentrated to a solid, 2.1 g, m.p. 68°–70° C.

| ANALYSIS | | | |
|---|---|---|---|
| Calculated for $C_{13}H_{12}N_4$ | 69.62% C | 5.40% H | 24.98% N |
| Found | 68.98% C | 5.48% H | 24.79% N |

EXAMPLE 22

N-(4-Amino-3-pyridinyl)-1H-indazol-6-amine

To $PtO_2$ (0.3 g) in 10 ml of ethanol was added N-(4-nitro-3-pyridinyl)-1H-indazol-6-amine, $N^6$-oxide (2.0 g) in 240 ml of ethanol and this was hydrogenated on a Parr apparatus at 60 psi for 20 hours. The mixture was filtered and concentrated to an oil (2.1 g). This material was eluted with 20% methanol/DCM on a silica gel column via HPLC. The desired fractions were concentrated to a solid (0.7 g), which was recrystallized from acetonitrile to yield a solid 0.5 g, m.p. 214°–216° C.

| ANALYSIS | | | |
|---|---|---|---|
| Calculated for $C_{12}H_{11}N_5$ | 63.99% C | 4.92% H | 31.09% N |
| Found | 64.16% C | 4.92% H | 31.23% N |

We claim:

1. A compound having the formula

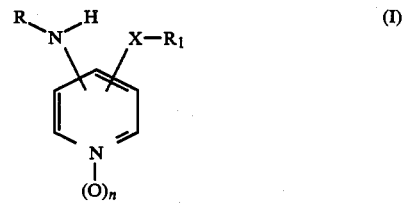

where
n is 0 or 1;
X is O or $NR_2$, $R_2$ being hydrogen, loweralkyl or loweralkylcarbonyl;
R is hydrogen, loweralkyl, arylloweralkyl or loweralkylcarbonyl; and
$R_1$ is

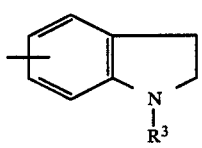

wherein $R_3$ is hydrogen, loweralkyl or loweralkylcarbonyl; the term aryl signifying a phenyl group optionally mono-substituted with a loweralkyl, loweralkoxy, halogen or trifluoromethyl group; or a pharmaceutically acceptable acid salt thereof.

2. The compound as defined in claim 1, where X is O or NH.

3. The compound as defined in claim 1, where R is hydrogen.

4. The compound as defined in claim 1, where X is O or NH, and R is hydrogen.

5. The compound as defined in claim 1, which is N-(4-amino-3-pyridinyl)-1H-indol-5-amine.

6. The compound as defined in claim 1, which is N-(4-amino-3-pyridinyl)-1-methyl-1H-indol-5-amine.

7. The compound as defined in claim 1, which is N-(3-amino-4-pyridinyl)-1H-indol-5-amine.

8. The compound as defined in claim 1, which is 3-[(1H-indol-5-yl)oxy]-4-pyridinamine.

9. The compound as defined in claim 1, which is 1-acetyl-N-(4-amino-3-pyridinyl)-2,3-dihydro-1H-indol-5-amine.

10. The compound as defined in claim 1, which is 4-[(1H-indol-5-yl)oxy]-3-pyridinamine.

11. The compound as defined in claim 1, which is N-(4-amino-3-pyridinyl)-1H-indol-7-amine.

12. A compound having the formula,

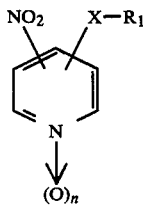

where
n is 0 or 1;
X is O or $NR_2$, $R_2$ being hydrogen, loweralkyl or loweralkylcarbonyl; and $R_1$ is

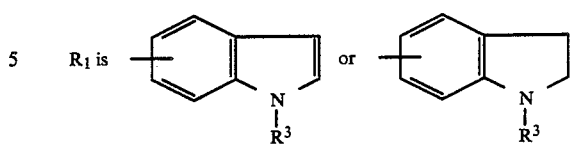

wherein $R_3$ is hydrogen, loweralkyl or loweralkylcarbonyl; or a pharmaceutically acceptable acid addition salt thereof.

13. The compound as defined in claim 12, where X is O or NH.

14. The compound as defined in claim 12, where n is 1.

15. The compound as defined in claim 12, where X is O or NH, and n is 1.

16. The compound as defined in claim 12, which is N-(4-nitro-3-pyridinyl)-1H-indol-5-amine, $N^5$-oxide.

17. The compound as defined in claim 12, which is 1-methyl-N-(4-nitro-3-pyridinyl)-1H-indol-5-amine, $N^5$-oxide.

18. The compound as defined in claim 12, which is N-(3-nitro-4-pyridinyl)-1H-indol-5-amine.

19. The compound as defined in claim 12, which is N-(4-nitro-3-pyridinyl)-1H-indol-7-amine, $N^7$-oxide.

20. The compound as defined in claim 12, which is 1-acetyl-2,3-dihydro-N-(4-nitro-3-pyridinyl)-1H-indole-5-amine, $N^5$-oxide.

21. The compound as defined in claim 12, which is 5-[(4-nitro-3-pyridinyl)oxy]-1H-indole, $N^5$-oxide.

22. The compound as defined in claim 12, which is 5-[(3-nitro-4-pyridinyl)oxy]-1H-indole.

23. A dermatological composition which comprises a compound as defined in claim 1 in an amount effective for treating a skin disorder, and a suitable carrier therefor.

24. A dermatological composition which comprises a compound as defined in claim 12 in an amount effective for treating a skin disorder, and a suitable carrier therefor.

25. A method of treating a patient in need of relief from a skin disorder which comprises administering to such a patient an effective amount of a compound as defined in claim 1.

26. A method of treating a patient in need of relief from a skin disorder which comprises administering to such a patient an effective amount of a compound as defined in claim 12.

* * * * *